United States Patent [19]

Ross et al.

[11] Patent Number: 5,439,803
[45] Date of Patent: Aug. 8, 1995

[54] ISOTOPE AND ASSAY FOR GLYCOLYSIS AND THE PENTOSE PHOSPHATE PATHWAY

[75] Inventors: Brian D. Ross, Ann Arbor, Mich.; Peter B. Kingsley, Memphis, Tenn.

[73] Assignee: The Regents of the University of Michigan, Ann Arbor, Mich.

[21] Appl. No.: 124,514

[22] Filed: Sep. 20, 1993

Related U.S. Application Data

[63] Continuation-in-part of Ser. No. 106,172, Aug. 13, 1993, abandoned.

[51] Int. Cl.$^6$ .......................... C12P 19/02; C12Q 1/54; C12Q 1/48
[52] U.S. Cl. ....................................... 435/14; 435/15; 435/72; 435/105
[58] Field of Search .................. 435/72, 105, 183, 190, 435/194, 14, 15

[56] References Cited

U.S. PATENT DOCUMENTS 4,656,133  4/1987  Goux ..................................... 435/72

OTHER PUBLICATIONS

Wood H., The Distribution of $C^{14}$ in the Hexose Phosphates . . . J Biol Chem 233: 1279-1282 (1958).
Desage M., Positional Isotopic Analysis of $^{13}C$ . . . Biomed & Environ Mass Spec 18 pp. 1010-1015 1989.
Serianni A., Stable Isotopically Enriched D-Glucose . . . J Carbo Chem 9 (5) 513-541 1990.
Saur, W. K. et al., "Deuterium Isotope Effects in the Fermentation of Hexoses to Ethanol by *Saccharomyces cerevisiae*. I. Hydrogen Exchange in the Glycolytic Pathway," *Biochemistry* 7:3529-3536 (1968).
Saur, W. K. et al., "Deuterium Isotope Effects in the Fermentation of Hexoses to Ethanol by *Saccharomyces cerevisiae*. II. A Steady-State Kinetic Analysis of the Isotopic Composition of the Methyl Group of Ethanol in an Isotopic Mirror Fermentation Experiment," *Biochemistry* 7:3537-3546 (1968).
Wu, J. et al., "Multiply $^{13}C$-substituted monosaccharides: synthesis of D-(1,5,6-$^{13}C_3$)glucose and D-(2,5,6-$^{13}C_3$)glucose," *Carbohydr. Res.* 226:261-269 (1992).
Wood, H. G. et al., "The Distribution of $C^{14}$ in the Hexose Phosphates and the Effect of Recycling in the Pentose Cycle," *J. Biol. Chem.* 233:1279-1282 (1958).
Serianni A. S., et al., "Stable Isotopically-Enriched D-Glucose: Strategies To Introduce Carbon, Hydrogen And Oxygen Isotopes At Various Sited," *J. Carbohydr. Chem.* 9:513-541 (1990).
Longenecker, J. P. et al., "Use of [2-$^{14}C$]Glucose and [5-$^{14}C$]Glucose for Evaluating the Mechanism and Quantitative Significance of the 'Liver-Cell' Pentose Cycle," *Biochem. J.* 188:847-857 (1980).
Landau, B. R., et al., "A Quantitative Estimation of the Pathways of Glucose Metabolism in Rat Adipose Tissue in Vitro," *J. Biol. Chem.* 239:697-704 (1964).
Larrabee, M. G. "Evaluation of the pentose phosphate pathway from $^{14}CO_2$ data," *Biochem. J.* 272:127-132 (1990).
Landau, B. R. et al., "Estimations of Pathway Contributions to Glucose Metabolism and the Transaldolase Reactions," *J. Biol. Chem.* 241:741-749 (1966).

(List continued on next page.)

*Primary Examiner*—William H. Beisner
*Assistant Examiner*—Ralph Gitomer
*Attorney, Agent, or Firm*—Harness, Dickey & Pierce

[57] ABSTRACT

An isotopically substituted molecule D-(1,6-$^{13}C_2$,6,6-$^2H_2$)glucose and method of use is provided for measuring the relative activities of glycolysis and the pentose phosphate pathway (PPP). By using the isotope, labeled in the C1 and C6 positions, of the present invention, a single incubation of cells provides lactate methyl groups derived from the C1 and C6 positions of the labeled isotope, which are distinguishable by gas chromatography/mass spectrometry (GC/MS). When combined with standard microdialysis techniques, the isotope and method of the present invention may also be used to monitor in vivo glycolysis and the PPP.

9 Claims, 4 Drawing Sheets

OTHER PUBLICATIONS

Landau, B. R. et al., "Estimation of Pathway Contributions to Glucose Metabolism and of the Rate of Isomerization of Hexose 6–Phosphate," *J. Biol. Chem.* 239:686–696 (1964).

Katz, J. et al., "The Use of Glucose-$C^{14}$ for the Evaluation of the Pathways of Glucose Metabolism," *J. Biol. Chem.* 235:2165–2177 (1960).

Katz, J. et al., "The Labeling of Pentose Phosphate from Glucose-$^{14}$C and Estimation of the Rates of Transaldolase, Transketolase, the Contribution of the Pentose Cycle, and Ribose Phosphate Synthesis," *Biochemistry* 6:2227–2247 (1967).

Kingsley-Hickman, P. B. et al., "Hexose Monophosphate Shunt Measurement in Cultured Cells with [1-$^{13}$C]Glucose: Correction for Endogenous Carbon Sources Using [6-$^{13}$C]Glucose," *Anal. Biochem.* 185:235–237 (1990).

King-Morris, M. J. et al., "Stable, Isotopically Substituted Carbohydrates: An Improved Synthesis of (6-$^{13}$C)Aldohexoses," *Carbohydr. Res.* 175:49–58 (1988).

Cheng, H-M. et al., "Proton NMR Spectroscopy of Glucose Consumption by Cultured Lens Spithelial Cells," *J. Ocular Pharmacol.* 2:319–324 (1986).

Wood, H. G. et al., "Estimation of Pathways of Carbohydrate Metabolism," *Biochem. Z.* 338:809–847 (1963).

Loreck, D. J. et al., "Regulation of the Pentose Phosphate Pathway in Human Astrocytes and Gliomas," *Metabol. Brain Dis.* 31–46 (1987).

Larrabee, M. G., "The Pentose Cycle (Hexose Monophosphate Shunt)," *J. Biol. Chem.* 264:15875–15879 (1989).

Katz, J. et al., "The Pentose Cycle, Triose Phosphate Isomerization, and Lipogenesis in Rat Adiopose Tissue," *J. Biol. Chem.* 241:727–740 (1966).

Horecker, B. L., et al., "The Mechanism of Pentose Phosphate Conversion to Hexose Monophosphate," *J. Biol. Chem.* 207:393–403 (1954).

McKeehan, W. L., "Glycolysis, Glutaminolysis and Cell Proliferation," *Cell Biol. Int. Rep.* 6:635–650 (1982).

Miceli, M. V. et al., "Glucose Uptake, Hexose Monophosphate Shunt Activity, and Oxygen Consumption in Cultured Human Retinal Pigment Epithelial Cells," *Invest. Opthalmol. Vis. Sci.* 277–283 (1990).

Mitchell, S. L. et al., "Gas Chromatographic-Mass Spectrometric Analysis Of Hexose Monophosphate Shunt Activity In Cultured Cells," *Biochem. Biophys. Res. Commun.* 158:474–479 (1989).

Jolley, R. L. et al., "Glucose Catabolism in Fetal and Adult Heart," *J. Biol. Chem.* 233:1289–1294 (1958).

Jarrett, R. J. et al., "Glucose Metabolism of Isolated Mammalian Islets Of Langerhans," *Lancet* 1:633–635 (1966).

Hothersall, J. S. et al., "Alternative Pathways of Glucose Utilization in Brain. Changes in the Pattern of Glucose Utilization in Brain during Development and the Effect of Phenazine Methosulfate on the Integration of Metabolic Routes," *Arch. Biochem. Biophys.* 198:478–492 (1979).

Heinze, E., et al., "Glucose Metabolism of Isolated Pancreatic Islets: Difference Between Fetal, Newborn and Adult Rats," *Endocrinology* 88:1259–1263 (1971).

Green, M. R. et al., "Contribution of the Pentose Cycle to Glucose Metabolism in Muscle," *Arch. Biochem. Biophys.* 111:569–575 (1965).

Nathan, et al., "Antitumor Effects of Hydrogen Peroxide in Vivo," *J. Exp. Med.* 154:1539–1553 (1980).

Halliwell, B. et al., "Exygen toxicity, oxygen radicals, transition metals and disease," *Biochem. J.* 219:1 (1984).

Pyatak, P S. et al., "Preparation of a Polyethylene Glycol: Superoxide Dismutase Adduct, and an Examination of its Blood Circulating Life and Anti–Inflammatory Activity," *Res. Commun. Chem. Pathol. Pharmacol.* 29:113 (1980).

Okada, H. et al., "Pharmacokinetics of Once–a–Month Injectable Microspheres of Leuprolide Acetate," *Pharm. Res.* 8:787 (1991).

Hora, M. S. et al., "Release of Human Serum Albumin from Poly(lactide-co-glycolide) Microspheres[1]," *Pharm. Res.* 7:1190 (1990).

Abuchowski, A. et al., "Alteration of Immunological Propertie of Bovine Serum Albumin by Covalent Attachment of Polyethylene Glycol," *J. Biol. Chem.* 252:3578 (1977).

Willis J. A. et al., "Dynamic Assessment of Hexose Monophosphate Shunt Activity in the Intact Rabbit Lens by Proton NMR Spectroscopy," *Biochem. Biophys. Res. Commun.* 138:1068–1073 (1986).

(List continued on next page.)

OTHER PUBLICATIONS

Tserng, K.-Y. et al., "Determination of Carbon-13 Labeled Lactate in Blood by Gas Chromatography/Mass Spectrometry," *Anal. Chem.* 56:517–523 (1984).

Ross, B. D. et al. "Carbohydrate Metabolism of the Rat C6 Glioma. An in vivo $^{13}$C and in vitro $^1$H Magnetic Resonance Spectroscopy Study," *NMR Biomed.* 1:20–26 (1988).

Prichard, J. W. et al., "Cerebral metabolic studies in vivo by $^{31}$P NMR," *PNAS (USA)* 80:2748 (1983).

Newmark, R. D. et al., "$^3$H nuclear magnetic resonance study of anaerobic glycolysis in packed erythrocytes," *P.N.A.S. (USA)* 87:583–587 (1990).

London, R. E. et al., "A Deuterium Surface Coil NMR Study of the Metabolism of D-Methionine in the Liver of the Anesthetized Rat," *Biochem.* 27:7869 (1988).

Schmidt, O. T. "Isopropylidene Derivatives," *Meth. Carbohydr. Chem.* vol. II, 318–325 (1963).

Rubinstein, L. V. et al., "Comparison of In Vitro Anticancer-Drug-Screening Data Generated With a Tetrazolium Assay Versus a Protein Assay Against a Diverse Panel of Human Tumor Cell Lines," *J. Natl. Cancer. Inst.* 82:1113 (1990).

Robinson, J. L. et al., "The Proton Transfer Reactions of Muscle Pyruvate Kinase," *J. Biol. Chem.* 247:1096–1105 (1972).

"Enzyme Nomenclature," Academic Press, pp. 56–115 (1992).

Ben-Yoseph, O. et al., "Metabolic Loss of Deuterium from Isotopically Labled Glucose," *Magn. Reson. Med.* 32(3):405–409 (1994).

Ross, B. D., et al., "Measurement of Pentose Phosphate-Pathway Activity in a Single Incubation with [1,6-$^{13}$C$_2$,6,6-$^2$H$_2$)glucose," *Biochem. J.* 302:31–38 (1994).

Willis J. A., et al., "Dynamic Assessment of Hexose Monophosphate Shunt Activity in the Intact Rabbit Lens by Proton NMR Spectroscopy," *Biochem. Biophys. Res. Commun.* 138(3):1068–1073 (1986).

ISOTOPE AND ASSAY FOR GLYCOLYSIS AND THE PENTOSE PHOSPHATE PATHWAY

SPONSORSHIP

Work on this invention was supported in part by a Research Investigation Grant from the American Cancer Society (Grant #BE-149), an Institutional Research Grant (#IN-40-32) to the University of Michigan Cancer Center from the American Cancer Society, the National Institutes of Health Grants P20 NS31114, R29 CA59009 and R29 HL42168, and the American Lebanese Syrian Associated Charities (ALSAC). The government has certain rights in this invention.

RELATED APPLICATIONS

This is a continuation-in-part application of U.S. Ser. No. 08/106,172 filed Aug. 13, 1993, by Brian D. Ross, now abandoned.

FIELD OF THE INVENTION

The present invention relates generally to a novel isotope and method of measuring the activity of glycolysis and the pentose phosphate pathway (PPP) and, more particularly, to a stable isotope D-(1,6-$^{13}C_2$,6,6-$^2H_2$)glucose and methods of its use to assay for the products of glycolysis and the PPP.

BACKGROUND OF THE INVENTION

The pentose phosphate pathway (PPP) is an important pathway for protecting cells from oxidative stress. The PPP will typically be stimulated in response to oxygen radical formation from such things as exposure to xenobiotics and radiation.

The oxidative branch of the pentose phosphate pathway produces ribose-5-P, $CO_2$ and NADPH from glucose-6-phosphate (Glc-6-P) and NADP+ and water. Glc-6-P is converted from glucose by the enzyme hexokinase. (See FIG. 2 for synthesis scheme.) Katz, J. et al., *J. Biol Chem.* 235:2165–2177 (1960) and Wood, H. G. et al., *Biochem. Z.* 338:809–847 (1963). NADPH can be used for lipid synthesis and antioxidant defense, and ribose-5-P can be used for nucleotide formation. The ribose-5-P can also be converted by the nonoxidative branch of the PPP to fructose-6-P (Fru-6-P) and glyceraldehyde-3-P, which can then be converted to lactate by glycolytic enzymes. Fru-6-P can also recycle through the PPP. Alternatively, lactate is produced via glycolysis without following the PPP, specifically, Glc-6-P (converted from glucose) can convert to Fru-6-P and glyceraldehyde-3-P without first converting to ribose-5-P. Since both pathways utilize Glc-6-P of the PPP, and ribose-5-P of the PPP converts to Fru-6-P of the glycolytic pathway, the pathways are considered coupled.

Activity of the PPP is commonly quantitated by measuring $^{14}CO_2$ production from the C1 of [1-$^{14}$C]glucose. A parallel incubation with [6-$^{14}$C]glucose is required to correct for $^{14}CO_2$ production from the citric acid cycle. Katz, J. et al., *J. Biol. Chem.* 235:2165–2177 (1960); Wood, H. G. et al., *Biochem. Z.* 338:809–847 (1963); Katz, J. et al., *J. Biol. Chem.* 241:727–740. (1966) and Hothersall, J. S. et al., *Arch. Biochem. Biophys.* 198:478–492 (1979). This method has various limitations such as extensive Krebs cycle activity producing large amounts of $^{14}CO_2$ from both [1-$^{14}$C]glucose and [6-$^{14}$C]glucose, thus making it difficult to quantitate low levels of PPP activity. Jolley, R. L. et al., *J. Biol. Chem.* 233:1289–1294 (1958), In addition, only a single measurement can be made on each sample because the sample must be destroyed by acidification to release $CO_2$. Two parallel incubations with [1-$^{14}$C]glucose and [6-$^{14}$C]glucose must also be performed for each measurement with intersample variability increasing the uncertainty of the data. Furthermore, calculations of PPP activity require measuring the amount of glucose consumed. Wood, H. G. et al., *Biochem. Z.* 338:809–847 (1963); Katz, J. et al., *J. Biol. Chem.* 241:727–740 (1966) and Hothersall, J. S. et al., *Arch. Biochem. Biophys.* 198:478–492 (1979).

Although the first two limitations can be overcome by measuring the isotopic composition of triose phosphate derivatives such as lactate rather than $CO_2$ (Katz, J. et al., *J. Biol. Chem.* 235:2165–2177 (1960); Wood, H. G. et al., Biochem. Z. 338:809–847 (1963) and Katz, J. et al., *J. Biol. Chem.* 241:727–740 (1966)), efforts to quantitate PPP activity in a single incubation by measuring (3-$^{13}$C)lactate and (3-$^{12}$C)lactate produced from (1-$^{13}$C)glucose have been complicated by an unknown amount of (3-$^{12}$C)lactate produced from endogenous (unlabeled) substrates. Willis, J. A. et al., *Biochem. Biophys. Res. Commun.* 138:1068–1073 (1986); Cheng, H-M. et al., *J. Ocular Pharmacol.* 2:319–324 (1986); Ross, B. D. et al. NMR Biomed. 1:20–26 (1988); Mitchell, S. L. et al., *Biochem. Biophys. Res. Commun.* 158:474–479 (1989) and Miceli, M. V. et al., *Invest. Opthalmol. Vis. Sci.* 277–283 (1990). Thus, a parallel incubation with (6-$^{13}$C)glucose is required. Kingsley-Hickman, P. B. et al., *Anal. Biochem.* 185:235–237 (990).

It would thus be desirable to provide an isotope and method for measuring or assaying the activities of the glycolysis and pentose phosphate pathway (PPP). It would also be desirable to provide an isotope and method for measuring the relative activities of glycolysis and the PPP which only requires a single incubation. It would further be desirable to provide an isotope and method for measuring glycolysis and PPP activity wherein repeated measurements can be made on a single sample. It would also be desirable to provide an isotope and method for measuring glycolysis and PPP activity which is not interfered by the presence of extensive $CO_2$. It would further be desirable to provide an isotope and method for measuring relative activities of glycolysis and the PPP which does not require the measurement of consumed glucose.

SUMMARY OF THE INVENTION

An isotopically substituted molecule D-(1,6-$^{13}C_2$,6,6-$^2H_2$)glucose is provided and used for quantifying the activities of glycolysis and the pentose phosphate pathway (PPP) by measuring labeled lactate production. Herein, the PPP is defined as the sequence of reactions which generate NADPH when glucose 6-phosphate (Glc-6-P) is oxidized to ribose 5-phosphate and which are coupled with and thus herein include glycolysis. Glycolysis herein is defined as the sequence of reactions that converts glucose into pyruvate with the concomitant production of ATP, including the conversion of pyruvate to lactate. A metabolic model, which allows for any degree of partial recycling of PPP products is also provided for calculating PPP activity from measurements of isotopically labeled lactate provided from labeled glucose.

By using the glucose labeled in the C1 and C6 positions in accordance with the present invention, a single incubation of cells provides lactate methyl groups, derived from the C1 and C6 positions, which are distinguishable by gas chromatography/mass spectrometry (GC/MS). Furthermore, because lactate containing C1 of the original glucose can be distinguished from lactate containing C6 of the original glucose, only a single incubation or exposure is required. In addition to monitoring glycolysis and the PPP in vitro, the isotope and method of the present invention may be combined with standard microdialysis techniques to monitor in vivo glycolysis and the PPP. The present invention can also be used to screen therapeutics, such as antioxidative enzyme inhibitors and/or monitor treatment. Thus, treatments involving the PPP such as administration of oxidative stress to cancer patients, e.g. the oxidation therapy of U.S. Ser. No. 08/106,172, may be monitored by the present invention.

Using the isotope and method of the present invention, any enzyme system capable of glycolysis and PPP can be assayed for the lactate product of these pathways. Thus, the present invention is applicable to both in vivo and in vitro systems, including cell-free systems (e.g. enzymatic solutions).

The method of the present invention, utilizing the isotope of the present invention, has various advantages over the traditional method in which $^{14}CO_2$ production from [$1-^{14}C$]glucose and [$6-^{14}C$]glucose is compared. For example, extensive $CO_2$ production by Krebs cycle activity does not interfere with the measurements; repeated measurements can be made on a single set of cells; a single incubation is required; it is not necessary to measure the amount of glucose consumed in order to calculate relative activities of glycolysis and the PPP; and the PPP can be measured in situ.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
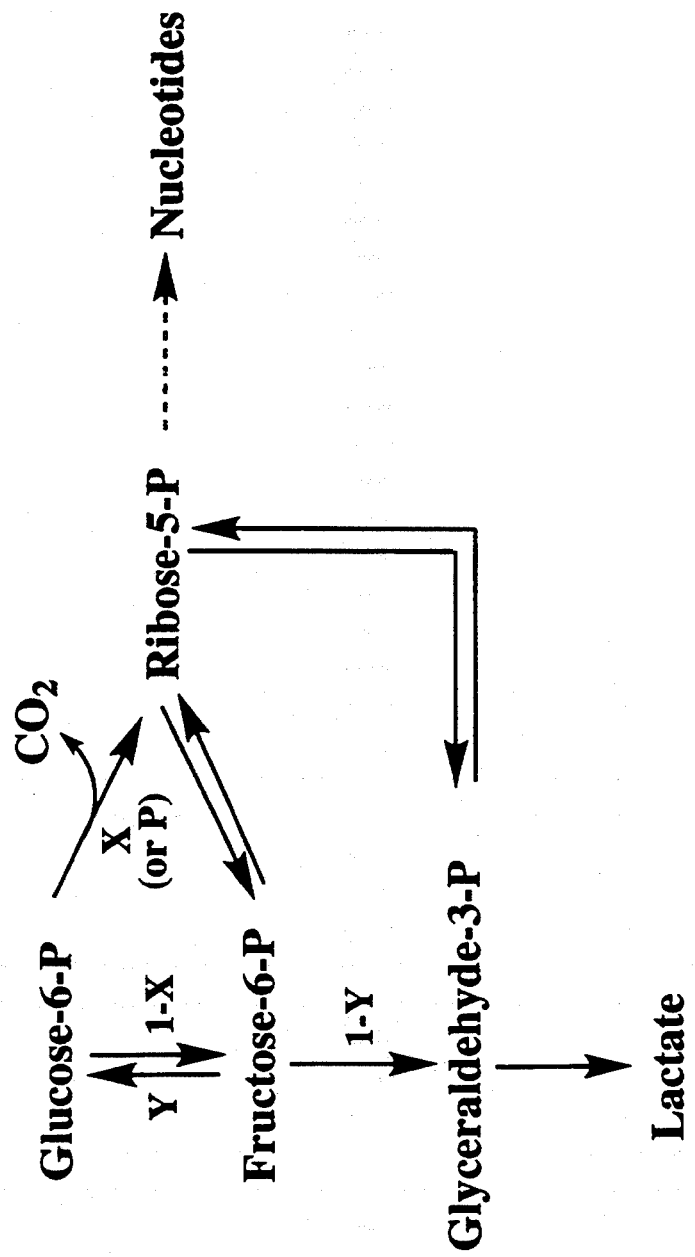
FIG. 1 is a flow chart depicting the biochemical model used for calculation of cellular PPP activity.

A multiply labeled isotope D-$(1,6-^{13}C_2,6,6-^{2}H_2)$glucose is provided for detecting and measuring the products and thus activities of glycolysis and the pentose phosphate pathway (PPP). Metabolism of D-$(1,6-^{13}C_2,6,6-^{2}H_2)$glucose through glycolysis produces $(3-^{13}C)$lactate (m+1) and $(3-^{13}C,3,3-^{2}H2)$lactate (m+3), whereas metabolism through the PPP produces $(3-^{13}C,3,3-^{2}H_2)$lactate (m+3). Thus, lactate produced by glycolysis from the labeled glucose of the present invention will be labeled C1 and C6, whereas lactate produced from the PPP will either be unlabeled or labeled from the bottom half of the glucose molecule, i.e. C6. Because lactate containing C1 of the original glucose can be distinguished from lactate containing C6 of the original glucose, only a single incubation with the isotope is required. Furthermore, because the PPP activity is quantitated by measuring labels in lactate, not labels in $CO_2$, extensive $CO_2$ production from Krebs cycle activity does not interfere and multiple measurements can be made on each sample because the sample is not acidified to release $CO_2$. Also, the relative activities of glycolysis and the PPP can be calculated without measuring net glucose utilization or lactate production.

Additionally, the present invention is not limited to in vitro analysis. The isotope, D-$(1,6-^{13}C_2,6,6-^{2}H_2)$glucose of the present invention can, for example, be infused and the labeled lactate removed by conventional intracerebral microdialysis techniques. Thus, regional glycolysis and PPP measurement can be made in vivo, e.g. in brains of conscious animals. Thus, treatment involving the PPP such as administration of oxidative stress to cancer patients, such as the oxidation therapy of U.S. Ser. No. 08/106,172, may be monitored by the method of the present invention. In addition to monitoring treatments, the present invention can be used to screen therapeutics. For example, the effectiveness of antioxidant enzyme inhibitors can be evaluated. See e.g., Specific Examples 1 and 2.

Comparisons with the method of the present invention utilizing $(1-^{13}C)$glucose and $(6-^{13}C)$glucose (Kingsley-Hickman, P. B. et al.,Anal Biochem. 185:235-237 (1990)) have also indicated that $(6-^{13}C, 1,6,6-^{2}H_3)$glucose and $(1,5,6-^{13}C_3)$glucose are ineffective in quantitating PPP activity. Formulas for calculating PPP activity from GC/MS measurements of lactate produced from glucose labeled in the C1 and/or C6 positions are also set forth below.

The following Specific Examples further describe the present invention.

SPECIFIC EXAMPLE 1

Synthesis of Glucose Isotopes.

All isotopically substituted D-glucose molecules were produced in accordance with the present invention by Omicron Biochemicals, Inc. (South Bend, Ind.), and their atom percent enrichments were determined using high-resolution $^1H$ and $^{13}C$ NMR spectroscopy and GC/MS. The synthesis of $(1,5,6-^{13}C_3)$glucose has been reported, (Wu, J. et al., Carbohydr. Res. 226:261-269 (1992)) and thus only a brief account of the preparation is given here.

D-$(1-^{13}C)$Glucose (Serianni A. S., et al., J. Carbohydr. Chem. 9:513-541 (1990)) was converted to 1,2-isopropylidene-α-D-$(1-^{13}C)$-glucofuranose (Schmidt, O. T. Meth. Carbohydr. Chem. Vol. II, 31 8-325 (1963)) and then to 1,2-O-isopropylidene-α-D-$(1-^{13}C)$-xylo-pentodialdo-1,4-furanose by periodate cleavage. King-Morris, M. J. et al., Carbohydr. Res. 175:49-58 (1988). This product was condensed with $K^{13}CN$ and the resulting cyanohydrins were reduced with $^{2}H_2$ to give an epimeric mixture of 1,2-O -isopropylidene-α-hexodialdo-1,4-furanoses having the D-gluco and L-ido configurations. This mixture was reduced with $NaB^{2}H_4$, and after hydrolysis and chromatography, D-$(1,6-^{13}C_2,6,6-^{2}H_2)$glucose was isolated in pure form and crystallized from absolute methanol.

Cell Culture Conditions.

Rat 9L glioma cells and human SF763 glioma cells were grown to confluence in 24-well flat bottom sterile tissue culture plates in minimum essential medium (MEM) containing 10% fetal bovine serum and antibiotics in a 5% $CO_2$/air incubator at 37° C. Immediately prior to incubation experiments, flasks were rinsed 3 times with Krebs-Ringer bicarbonate buffer (KRB), pH=7.4. Four replicate wells were used for each experimental condition. Each well was incubated for 1 hour with 0.5 ml KRB supplemented with an isotopically substituted glucose (5.5 or 2.8 mM) under the various conditions summarized in Table 1 below. Following the incubation, the buffer was removed and lyophilized for GC/MS analysis.

TABLE 1

Measurement of PPP Activity Under Various Conditions In Cultured 9L Glioma Cells

| Glucose Isotope(s) | Conditions | P (%)* |
|---|---|---|
| Experiment #1A: | | |
| (1-$^{13}$C) & (6-$^{13}$C)Glc | 5.5 mM | 7.1 ± 2.5 |
| (1-$^{13}$C) & (6-$^{13}$C)Glc | 5.5 mM + 5 μM PMS | 37.2 ± 2.9 |
| Experiment #1B: | | |
| (6-$^{13}$C,1,6,6-$^2$H$_3$)Glc | 5.5 mM | 28.9 ± 2.2 |
| Experiment #1C: | | |
| (1,5,6-$^{13}$C$_3$)Glc | 5.5 mM | −8.9 ± 2.6 |
| (1-$^{13}$C) & (5-$^{13}$C)Glc | 5.5 mM | 9.4 ± 2.3 |
| Experiment #1D: | | |
| (1,6-$^{13}$C$_2$,6,6-$^2$H$_2$)Glc | 5.5 mM | 9.4 ± 2.1 |
| (1,6-$^{13}$C$_2$,6,6-$^2$H$_2$)Glc | 2.8 mM | 9.4 ± 2.0 |
| (1,6-$^{13}$C$_2$,6,6-$^2$H$_2$)Glc | 2.8 mM + 5 μM PMS | 30.6 ± 1.9 |
| Experiment #2: | | |
| (1,6-$^{13}$C$_2$,6,6-$^2$H$_2$)Glc | 5.5 mM | 6.4 ± 0.3 |
| (1,6-$^{13}$C$_2$,6,6-$^2$H$_2$)Glc | 4.4 mM (80%) + 1.1 mM Glc (20%) | 5.8 ± 0.7 |
| (1,6-$^{13}$C$_2$,6,6-$^2$H$_2$)Glc | 5.5 mM + 5 μM PMS | 43.5 ± 1.8 |
| (1,6-$^{13}$C$_2$,6,6-$^2$H$_2$)Glc | 4.4 mM (80%) + 1.1 mM Glc (20%) + 5 μM PMS | 41.8 ± 3.6 |

*PPP values are expressed as means ± S.D. from four incubations for each of the different conditions as indicated.

Cultured cell PPP activities from incubations with newly synthesized glucose isotopes were compared to the PPP activity obtained from parallel incubations with (1-$^{13}$C)glucose and (6-$^{13}$C)glucose. Kingsley-Hickman, P. B. et al., *Anal Biochem.* 5:235-237 (1990). The following experiments were conducted to evaluate the stable glucose isotopes for quantification of PPP activity. All incubations in Experiments 1A-1D of Table 1 were done in parallel.

Gas Chromatography/Mass Spectrometry.

For GC/MS analysis, dried samples were converted to their trimethylsilyl (Me$_3$Si) derivatives by addition of 50 μL pyridine and 50 μL bis(trimethylsilyl)-trifluoroacetamide with 1% trimethylchlorosilane (Alltech Associates Inc., Deerfield, Ill.) and heated to 50° C. for 15 minutes before injection. Mass spectra were acquired on a Hewlett Packard GC/MS (Model 890/5971) in the selected ion monitoring mode on the m/z 219 through m/z 222 ions. These ions correspond to the loss of a methyl group from the Me$_3$Si derivative of lactic acid at an ionization energy of 70 eV. In order to correct for the "tail" produced by the isotopic composition of the Me$_3$Si lactate derivative, the expected isotopic composition of this derivative was calculated from standard values of natural isotope abundance (Ude, D. R., ed. *CRC Handbook of Chemistry and Physics*, 72nd Ed., CRC Press, Boca Raton (1991)): 98.9% $^{12}$C, 1.1% $^{13}$C, 99.985% $^1$H, 0.015% $^2$H, 99.76% $^{16}$O, 0.04% $^{17}$O, 0.2% $^{18}$O, 92.23% $^{28}$Si, 4.67% $^{29}$Si, and 3.10% $^{30}$Si. Adjustments were made for positions that contained a known $^{13}$C or $^2$H label derived from labeled glucose, and the resulting intensities in the m+0 through m+3 peaks are shown in Table 2 below. Calculations of the relative intensities of the peaks of the mass spectrum of the trimethylsilyl derivative of lactate with isotopically substituted atoms were based on standard values of natural isotope abundance (Lide, D. R., ed. *CRC Handbook of Chemistry and Physics*, 72nd Ed., CRC Press, Boca Raton (1991)). Lactate standards were checked routinely in order to evaluate the GC/MS performance.

TABLE 2

Correction Factors for GC/MS Data of Lactate with Specific Isotope Compositions
Relative amount In the mass + n peak

| Isotope | n = 0* | n = 1 | n = 2 | n = 3 | n ≥ 4 |
|---|---|---|---|---|---|
| $^{13}$C$_0$$^2$H$_0$ | 100 | 19.4 | 8.91 | 1.15 | 0.24 |
| $^{13}$C$_0$$^2$H$_1$ | 100 | 19.42 | 8.90 | 1.15 | 0.24 |
| $^{13}$C$_0$$^2$H$_2$ | 100 | 19.40 | 8.90 | 1.15 | 0.24 |
| $^{13}$C$_1$$^2$H$_0$ | 100 | 18.32 | 8.70 | 1.06 | 0.23 |
| $^{13}$C$_1$$^2$H$_1$ | 100 | 18.30 | 8.70 | 1.06 | 0.23 |
| $^{13}$C$_1$$^2$H$_2$ | 100 | 18.29 | 8.70 | 1.05 | 0.23 |
| $^{13}$C$_2$$^2$H$_0$ | 100 | 17.21 | 8.51 | 0.96 | 0.21 |

*In the absence of any isotopic substitution, n = 0 corresponds to m/z 219 (M$^+$-CH$_3$)

A HP-5 fused silica column (30 m×0.25 mm i.d.) with a 0.25 mm film thickness (Hewlett Packard, Wilmington, Del.) was used for gas chromatography with helium as the carrier gas. Derivatized samples (1 μl) were injected into the column through the standard split/splitless injection port operated in the split mode (40:1) at 270° C. The column temperature was programmed for 0.5 min at 55° C. followed by a temperature ramp at 15° C./min to 140° C. The temperature was then increased to 280° C. and held for 3 min. GC/MS quantitation of the m/z 219 through m/z 222 ions was performed on triplicate injections of each individual sample. PPP activity was calculated for each injection and the average value of the PPP activity for each sample was used in error analysis. All data in Table 2 are expressed as the mean of multiple samples ±S.D.

Metabolic Model: Definition of PPP Activity.

PPP activity can be defined in two ways, which differ if the products can recycle through the pathway. One definition counts ⅓ the number of moles of $CO_2$ produced by the PPP per mole of glucose metabolized to lactate and/or $CO_2$. Katz, J. et al., *J. Biol. Chem.* 235:2165-2177 (1960). This definition is represented in Table 3 below by the sum of [0]$CO_2$ ($CO_2$ containing neither C1 nor C6 of the original labeled glucose)+[C1]$CO_2$ ($CO_2$ containing C1 of the original labeled glucose), and will be referred to as total PPP activity, or T. By this definition, T corresponds to the "% Pentose Cycle" or PC of several earlier papers (Katz, J. et al., *J. Biol Chem.* 235:2165-2177 (1960); Wood, H. G. et al., *Biochem. Z.* 338:809-847 (1963); Katz, J. et al., *J. Biol. Chem.* 241:727-740 (1966)) or $F_{met.}$ of Larabee. Larrabee, M. G. *Biochem J.* 272:127-132 (1990). In Table 3 values represent lactate equivalents of product (1 mole of lactate or 3 moles of $CO_2$) per mole of labeled glucose degraded to $CO_2$ and lactate by glycolysis and the PPP. The second definition counts only the $CO_2$ produced the first time a Glc-6-P molecule passes the first irreversible step in the PPP or glycolysis; recycling of the PPP products is not included. This definition is represented by P as depicted in FIG. 1 and Table 3 and corresponds to S or 1-γ of Katz et al. (Katz, J. et al., *J. Biol. Chem.* 241:727-740 (1966)) or $F_{ent.}$ of Larrabee. Larrabee, M. G. *Biochem. J.* 272:127-132 (1990)(20). In FIG. 1, $P = X/[X+(1-X)(1-Y)]$ which represents the percentage of glucose metabolized to lactate that loses C1 as $CO_2$ by PPP activity and Y represents the percentage of fructose 6-phosphate from the PPP that returns to glucose 6phosphate before being metabolized further by either the PPP or glycolysis. These two definitions would differ by a factor of exactly 3 if recycling did not occur, and the factor is slightly less than 3 if P is small.

TABLE 3

Labeled and Unlabeled Metabolic Products from Isotopically Substituted Glucose Molecules

| Product | Amount Produced |
|---|---|
| [C1]$CO_2$ | P/3 |
| [0]$CO_2$ | (2P/3)[PY/(3 − 2PY)] |
| [0]lactate | (2P/3)[(3 − 3PY)/(3 − 2PY)] + E |
| [C1]lactate | 1-P |
| [C6]lactate | 1 |

Metabolic Model PPP Calculation.

The model utilized for PPP calculation in FIG. 1 is similar to that of Landau et al. Landau, B. R. et al., *J. Biol. Chem.* 239:686-696 (1964). Although that model allows for partial recycling of PPP products, in practice the assumption of either no recycling or complete recycling has been used in the past. Katz, J. et al., *J. Biol. Chem.* 235:2165-2177 (1960); Katz, J. et al., *J. Biol. Chem.* 241:727-740 (1966) and Hothersall, J. S. et al., *Arch. Biochem. Biophys.* 198:478-492 (1979). The present model, while similar in some ways to earlier models, easily allows for any degree of partial recycling. The formulas of Landau et al. (Landau, B. R. et al., *J. Biol. Chem.* 239:686-696 (1964)) can be converted to the present formulas by the following substitutions: $E_{-h}/(1-PC)=Y/(1-Y)$ ; $V_1/V_h=X/(1-X)$; $G_2=L_{C2}$; $f=V_3=0$; $PC=T$.

Calculation of PPP activity in cells or tissues from the metabolism of glucose labeled in the C1 and/or C6 positions by NMR spectroscopy (Willis, J. A. et al., *Biochem. Biophys. Res. Commun.* 138:1068-1073 (1986); Cheng, H. M. et al., *J. Ocular Pharmacol.* 2:319-324 (1986); Ross, B. D. et al. *NMR Biomed.* 1:20-26 (1988); Mitchell, S. L. et al., *Biochem. Biophys. Res. Commun.* 158:474-479 (1989) and Miceli, M. V. et al., *Invest. Opthalmol. Vis. Sci.* 277-283 (1990)) or by GC/MS (Mitchell, S. L. et al., *Biochem. Biophys. Res. Commun.* 158:474-479 (1989) and Kingsley-Hickman, P. B. et al., *Anal. Biochem.* 185:235-237 (1990)) depends on the ability to detect and distinguish between labeled and unlabeled lactate. The lactate methyl group will be derived from either the C1 of the labeled glucose ([C1]lactate), the C6 of labeled glucose ([C6]lactate), or neither ([0]lactate). The model presented in FIG. 1 includes a parameter for PPP activity (X, or P) and allows the use of an estimate of recycling (Y) in calculating PPP activity. It also permits the estimation of unlabeled (endogenous) lactate precursors (E in Table 3). The relative amounts of labeled and unlabeled $CO_2$ and lactate, expressed as lactate equivalents, are shown as a function of P and Y (Table 3).

Formulas for determination of P, T, and E from experimental data are shown in Table 4. In Table 4 the parameters $R_1$ and $R_6$ are measured from experimental data and the formulas given under "Definition". The parameters P, T, and $r_6$ are calculated from the values of $R_1$ and $R_6$ and the formulas given under "Equal to". Because Y is not easily measured and must be estimated, values for T must be estimated from the formula in Table 4. For small values of P, the uncertainty in T will be small, but this uncertainty can become considerable at higher values of P. Y is probably large (Landau, B. R., et al., *J. Biol. Chem.* 239:697-704 (1964)) but must be less than 1.

TABLE 4

Formulas for Analysis of Experimental Data

| Parameter | Definition | Equal to |
|---|---|---|
| $R_1$ | [C1]lactate/{[0] + [C1] + [C6]}lactate | (1-P)/2 + E − T |
| $R_6$ | [C6]lactate/{[0] + [C1] + [C6]}lactate | 1/(2 + E − T) |
| P | X/[X + (1 − X)(1 − Y)] | 1 − $R_1/R_6$ |
| T | [0]$CO_2$ + [C1]$CO_2$ | P/(3 − 2PY) |
| $r_6$ | {[0] + [C1]}lactate/[C6] lactate | 1 + E − T |

The isotopes of lactate formed from the labeled glucoses utilized in the present study are summarized in Table 5 below. In Table 5, the indicated products do not include the possible loss of $^2H$ as described above. This assumes metabolism through glycolysis and that labels are not scrambled by metabolism beyond pyruvate or lactate.

TABLE 5

Labeled Lactate Molecules Derived from Different Isotopically Substituted Glucoses

| Label In Glucose | Label In [C1]lactate | Label In [C6]lactate |
|---|---|---|
| 1-$^{13}C$ | 3-$^{13}C$ | none |
| 6-$^{13}C$ | none | 3-$^{13}C$ |
| 1,5,6-$^{13}C_3$ | 3-$^{13}C$ | 2,3-$^{13}C_2$ |
| 1-$^{13}C$,1-$^2H$ | 3-$^{13}C$,3-$^2H$ | none |
| 6-$^{13}C$,6,6-$^2H_2$ | none | 3-$^{13}C$,3,3-$^2H_2$ |
| 6-$^{13}C$,1,6,6-$^2H_3$ | 3-$^2H$ | 3-$^{13}C$,3,3-$^2H_2$ |
| 1,6-$^{13}C_2$,6,6-$^2H_2$ | 3-$^{13}C$ | 3-$^{13}C$,3,3-$^2H_2$ |

Derivation of Equations and Formulas in Tables 3 and 4.

FIG. 1 depicts the metabolic model of the present invention. The originally proposed non-oxidative branch of the PPP is assumed (Horecker, B. L., et al., *J. Biol. Chem.* 207:393-403 (1954)) rather than the more recently proposed L-type pathway. Longenecker, J. P. et al., *Biochem. J.* 188:847-857 (1980). For each mole of glucose phosphorylated to Glc-6-P, X moles are oxidized irreversibly by Glc-6-P dehydrogenase, ultimately producing X moles (X/3 lactate equivalents) of $CO_2$ from C1 of Glc-6-P, 2X/3 moles of Fru-6-P containing C6 of Glc-6-P, and X/3 moles of glyceraldehyde-3-P containing C6 of Glc-6-P. The remaining 1−X moles of the initial Glc-6-P are converted to Fru-6-P. Other fates of Glc-6-P, primarily Glcl P for synthesis of glycogen or galactose, are not considered because they will not significantly affect the ratio of [C1]lactate to [C6]lactate produced (see discussion below).

For each mole of Fru-6-P produced, 1−Y moles are converted (irreversibly) to Fru(1,6)$P_2$ and then via triose phosphates to lactate, while the remaining Y moles are reconverted to Glc-6-P. Thus for each mole of Glc-6-P, X moles are metabolized via the PPP, (1−X)(1−Y) moles are metabolized via glycolysis, and (1−X)Y moles are reconverted to Glc-6-P. These (1−X)Y moles of reconverted Glc-6-P may continue to cycle back and forth between Glc-6-P and Fru-6-P, but eventually they will enter either the PPP or the irreversible step of glycolate (to Fru(1,6)$P_2$) in the same ratio as the initial Glc-6-P entered the pathways. The net result is that for each mole of glucose metabolized to lactate and $CO_2$, the PPP fraction is $$P = X/[X + (1-X)(1-Y)] \quad (1)$$

and the glycolytic fraction is $(1-X)(1-Y)/[X+(1-X)(1-Y)]$.

The glyceraldehyde-3-P produced by the PPP is assumed to proceed to lactate. Of the 2P/3 moles of Fru-6-P produced by the PPP, YP(2P/3) moles will return to the PPP, producing (YP/3)(2P/3) lactate equivalents of [0]$CO_2$ (along with more unlabeled Fru-6-P); $(1-Y)(2P/3)$ moles will proceed through glycolysis to lactate; and $Y(1-P)(2P/3)$ moles will return to Glc-6-P before being metabolized through glycolysis to lactate. The newly produced Fru-6-P will follow the same fates, eventually producing the results in Table 3. (It is assumed that Fru-6-P produced from PPP and from glycolysis are metabolized identically, with neither intracellular nor intercellular compartmentation.)

The C6 of the labeled glucose cannot become incorporated into the C1 of hexose phosphates (formation of Fru(1,6)$P_2$ is assumed to be irreversible) and therefore cannot be lost in the PPP. Transaldolase can incorporate C1 of glucose (via glyceraldehyde-3-P) into C6 of Fru-6-P (Landau, B. R. et al., *J. Biol. Chem.* 241:741–749 (1966)), but this will not affect the results because the C6 atoms ultimately appear in lactate, and the glyceraldehyde-3-P would also have appeared in lactate.

Standard PPP Measurements with (1-$^{13}$C)Glucose and (6-$^{13}$C)Glucose.

Glioma cells were incubated with KRB containing (1-$^{13}$C)glucose or (6-$^{13}$C)glucose with and without 5 μM phenazine methosulfate (PMS), which stimulates PPP activity by oxidizing NADPH to $NADP^+$. Hothersall, J. S. et al., *Arch. Biochem. Biophys.* 198:478–492 (1979).

Parallel incubations with (1-$^{13}$C)glucose and (6-$^{13}$C)glucose can be utilized to measure PPP activity in cultured cells. Kingsley-Hickman, P. B. et al., *Anal. Biochem.* 185:235–237 (1990). The PPP activity measured in cultured glioma cells was stimulated from 7.1±2.5% to 37.2±2.9% by 5 μM PMS (Experiment 1A in Table 1). With formulas for calculating the PPP using (1-$^{13}$C)glucose alone, neglecting unlabeled lactate precursors (Willis, J. A. et al., *Biochem. Biophys. Res. Commun.* 138:1068–1073 (1986)), the calculated PPP activities would have been 20.0±1.6% and 43.3±0.7%. These experiments further validate the use of parallel incubations with (1-$^{13}$C)glucose and (6-$^{13}$C)glucose to measure PPP activity. Kingsley-Hickman, P. B. et al., *Anal. Biochem.* 185:235–237 (1990).

Studies with (6-$^{13}$C,1,6,6-$^2$H$_3$)Glucose.

Glioma cells were incubated with (6-$^{13}$C,1,6,6-$^2$H$_3$)glucose. Parallel incubations with (1-$^{13}$C,1-$^2$H)glucose and (6-$^{13}$C,6,6-$^2$H$_2$)glucose were also done to investigate the extent of deuterium loss from the C1 and C6 positions of glucose.

In an attempt to measure PPP activity in a single incubation, a multiply labeled glucose molecule was sought which would produce two distinguishable lactate isotopomers when metabolized via the PPP and glycolysis, specifically one isotope from carbon atom C1 and the other from carbon atom C6. With (6-$^{13}$C,1,6,6-$^2$H$_3$)glucose, assuming no loss of $^2$H atoms unless the adjacent carbon atom is also lost, glycolysis yields (3-$^{13}$C,3,3-$^2$H$_2$)lactate and (3-$^2$H)lactate while metabolism through the PPP yields only (3-$^{13}$C,3,3-$^2$H$_2$)lactate as shown in Table 5 above.

One possibility for this discrepancy is the selective loss of $^2$H from C1 of glucose as it is metabolized to lactate. Such an exchange of $^2$H atoms from C1 of glucose with $^1$H atoms in water can be catalyzed by phosphomannose isomerase, which catalyzes the reversible formation of mannose 6-phosphate from fructose 6-phosphate. Saur, W. K. et al., *Biochemistry* 7:3529–3536 (1968) and Saur, W. K. et al., *Biochemistry* 7:3537–3546 (1968). The $^2$H atoms from C1 or C6 of glucose can also exchange with $^1$H atoms in water further down in the glycolytic pathway at the pyruvate kinase step (Robinson, J. L. et al., *J. Biol Chem.* 247:1096–1105 (1972)), and may exchange slowly from pyruvate via keto-enol tautomerization. The extent of exchange by these two mechanisms was tested by incubations with (6-$^{13}$C,6,6-$^2$H$_2$)glucose, which should lose $^2$H atoms only at the triose level and not via phosphomannose isomerase, and with (1-$^{13}$C,1-$^2$H)glucose, which can lose $^2$H via phosphomannose isomerase and at the triose level. In several different experiments with 9L glioma cells, values of $1-\kappa=0.06-0.13$ and $1-\mu=0.14-0.38$ were observed, where $1-\kappa$ is the fraction of $^2$H atoms lost from each position at C6 of glucose, presumably at the triose level, and $1-\mu$ is the additional fraction of $^2$H lost from C1 of glucose, presumably due to phosphomannose isomerase activity. Due to the inability of (6-$^{13}$C,1,6,6-$^2$H$_3$)glucose to quantitate PPP activity in a single incubation, studies using this isotopically substituted molecule were not pursued further.

Studies with (1,5,6-$^{13}$C$_3$)Glucose.

Glioma cells were incubated with (1,5,6-$^{13}$C$_3$)glucose and (5-$^{13}$C)glucose to check for selective loss of the C5 label. In a subsequent study, the ability of (1,5,6-$^{13}$C$_3$)glucose to measure changes in PPP activity was investigated by addition of 5 μM PMS.

In order to circumvent the complication caused by the loss of $^2$H atoms, an attempt was made to develop a multiply labeled glucose molecule which did not contain $^2$H atoms but which could still produce two distinguishable lactate isotopes when metabolized via the PPP and glycolysis. Metabolism of (1,5,6-$^{13}$C$_3$)glucose via glycolysis would yield equal amounts of (3-$^{13}$C)lactate and (2,3-$^{13}$C$_2$)lactate; metabolism via the PPP would yield only (2,3-$^{13}$C$_2$)lactate and some unlabeled lactate, as shown in Table 6 below. Thus, (2,3-$^{13}$C$_2$)lactate represents total glucose metabolized through glycolysis and PPP, while (3-$^{13}$C)lactate represents glucose metabolized via glycolysis. The difference is due to metabolism via the PPP.

TABLE 6

| Isotope Enrichment In Lactate Produced from (1,5,6-$^{13}$C$_3$)Glucose | | |
|---|---|---|
| m/z | Isotope | Amount In Lactate |
| 221 | $^{13}$C$_2$ | $L_{C5}L_{C6}$ |
| 220 | $^{13}$C$_1$ | $L_{C5}(1-L_{C6}) + L_{C6}(1-L_{C5}) + L_{C1}$ |
| 219 | $^{13}$C$_0$ | $(1-L_{C5})(1-L_{C6}) + (1-L_{C1})$ |

In Table 6 the amount of lactate with zero, one, or two $^{13}$C substitutions does not reflect loss of C1 by PPP activity or possible scrambling of the $^{13}$C labels by metabolism beyond pyruvate or lactate. $L_{C1}$, $L_{C5}$, and $L_{C6}$ refer to the fractional $^{13}$C enrichment in the C1, C5 and C6 atoms, respectively, of glucose.

In glioma cells incubated with (1,5,6-$^{13}$C$_3$)glucose, there was surprisingly more ($^{13}$C$_1$)lactate than ($^{13}$C$_2$)lactate, and the calculated PPP activity was −8.9±2.6%, significantly less than the value of 7.1±2.5% measured in parallel incubations with (1-$^{13}$C)glucose and (6-$^{13}$C)glucose (as shown in Experiment 1C of Table 1). In a separate study, measured PPP activity increased from approximately −12.3±0.3% to 16.9±1.2% when 51 μM PMS was added. Thus, although measurements with (1,5,6-$^{13}$C$_3$)glucose did not provide an accurate measurement of PPP activity, they did detect changes in PPP activity.

One potential complication in measurements with (1,5,6-$^{13}$C$_3$)glucose is the possibility that pyruvate may enter the Krebs cycle via pyruvate dehydrogenase and citrate synthase, and may later exit the cycle via phosphoenolpyruvate carboxykinase. The likelihood of such an event is suggested by the high level of glutaminolysis in glial cells, a process by which glutamine is converted to lactate via Krebs cycle intermediates. McKeehan, W. L., Cell. Biol. Int. Rap. 6:635–650 (1982). In a single pass through the cycle, (2,3-$^{13}$C$_2$)pyruvate would form (1,2-$^{13}$C)succinate and then a mixture of (1,2-$^{13}$C$_2$)oxaloacetate and (3,4-$^{13}$C$_2$)oxaloacetate. Decarboxylation of oxaloacetate would eventually produce (1,2-$^{13}$C)pyruvate and (3-$^{13}$C)pyruvate; in the latter case, the $^{13}$C is derived from the original C3 of pyruvate (derived from C6 of glucose), and the $^{13}$C in position C2 of pyruvate (from C5 of glucose) has been lost, To investigate whether selective loss of the 5-$^{13}$C label could account for our discordant results with (1,5,6-$^{13}$C$_3$)glucose, glioma cells were incubated with (1-$^{13}$C)glucose, (5-$^{13}$C)glucose, and (6-$^{13}$C)glucose in 3 parallel incubations. PPP activity was calculated with (1-$^{13}$C)glucose and either (5-$^{13}$C)glucose (P=9.4±2.3%) or (6-$^{13}$C)glucose (P=7.1±2.5%) (see Table 1). Clearly there was not selective loss of $^{13}$C from C5 of glucose, thus ruling out this explanation for the unexpected results from (1,5,6-$^{13}$C$_3$)glucose. Due to the inability of (1,5,6-$^{13}$C$_3$)glucose to quantitate PPP activity and the difficulties encountered in the synthesis of this isotope, PPP measurements using (1,5,6-$^{13}$C$_3$)glucose were not pursued further.

Studies with (1,6-$^{13}$C$_2$,6,6-$^2$H$_2$)Glucose. Rat 9L glioma cells were incubated with 5.5 and 2.8 mM (1,6-$^{13}$C$_2$,6,6-$^2$H$_2$)glucose alone or with 5 μM PMS.

Figure 2:
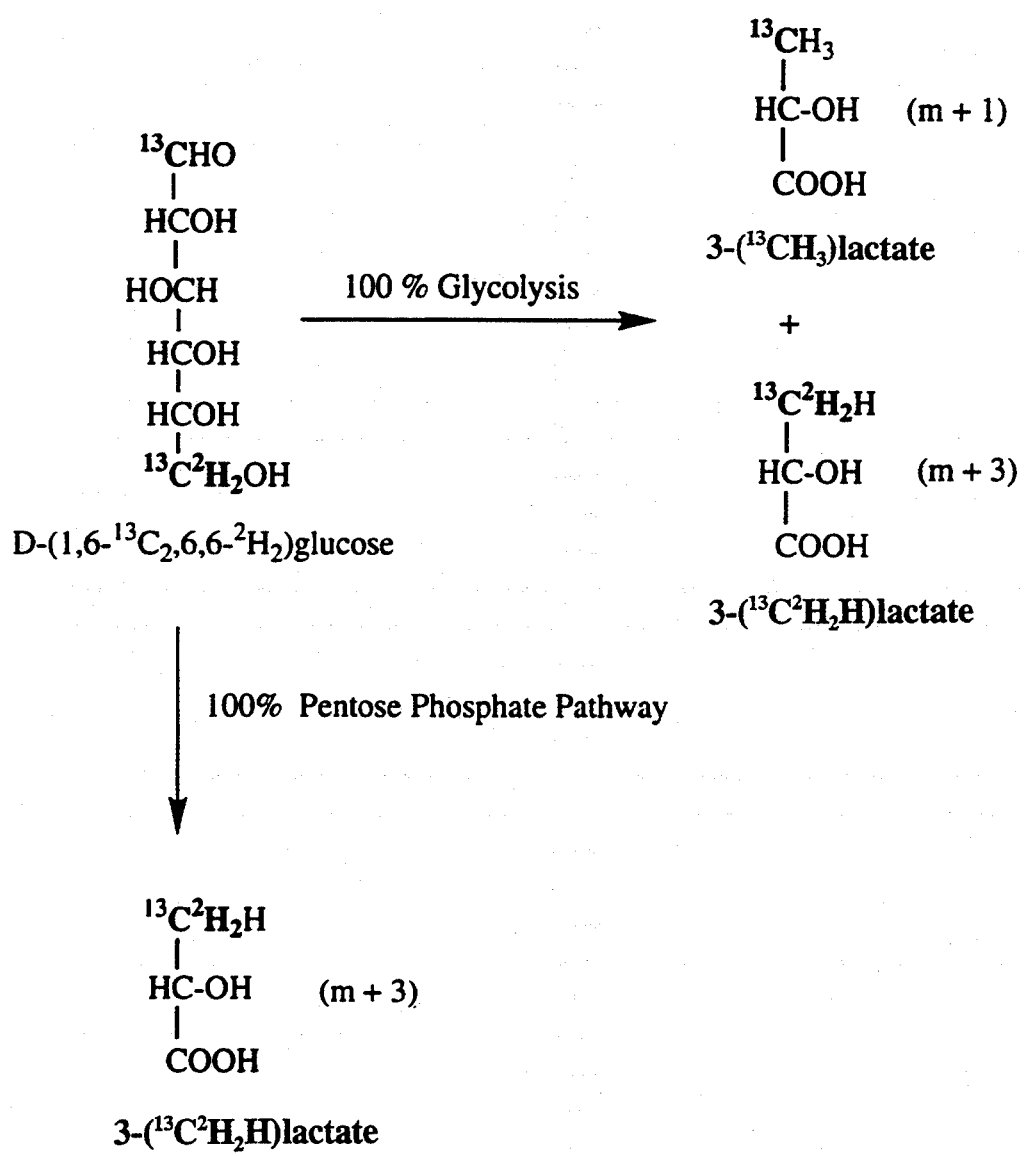
FIG. 2 is a flow chart depicting the biochemical rationale for the use of $(1,6-^{13}C_2,6,6-^{2}H_2)$glucose to quantitate PPP activity.

A glucose molecule labeled in only the C1 and C6 positions was sought that would not be affected by phosphomannose isomerase-catalyzed loss/exchange of $^2$H atoms. (1,6-$^{13}$C$_2$,6,6-$^2$H$_2$)Glucose differs from (6-$^{13}$C,1,6,6-$^2$H$_3$)glucose only in having $^{13}$C$^1$H instead of $^{12}$C$^2$H at position 1 of glucose, thus avoiding the large and variable loss of the $^2$H atom from C1 of glucose. FIG. 2 depicts that metabolism via glycolysis will produce a 1:1 mixture of (3-$^{13}$C$^2$H$_2$H)lactate:(3-$^{13}$CH$_3$)lactate, while degradation through the PPP will produce unlabeled lactate and (3-$^{13}$C$^2$H$_2$H)lactate. These two lactate products can be distinguished by either GC/MS or $^2$H NMR spectroscopy. The calculated PPP activity with (6-$^{13}$C,1,6,6-$^2$H$_3$)glucose, P=28.9±2.2%, was not consistent with the 7.1±2.5% PPP activity measured in parallel incubations with (1-$^{13}$C)glucose and (6-$^{13}$C)glucose. Measurements with (1,6-$^{13}$C2,6,6-$^2$H$_2$)glucose yielded 9.4±2.1% PPP activity, which was similar to the parallel incubations with (1-$^{13}$C)glucose and (6-$^{13}$C)glucose (Experiment 1D of Table 1). This activity was unchanged (9.4±2.0%) when the glucose concentration was halved, from 5.5 mM to 2.8 mM, and PPP activity increased to 30.6±1.9% when 5 μM PMS was added to the incubation medium.

Measurements of PPP activity with (1,6-$^{13}$C$_2$,6,6-$^2$H$_2$)glucose assume that $^2$H loss from each position is independent of $^2$H loss from the other position, so that the amount of [C6]lactate that has lost two $^2$H atoms can be calculated from the amount of lactate that has lost zero or one $^2$H atom (see Equation 13, below). (If this correction were not made, [C6]lactate that has lost both $^2$H atoms would appear as [C1]lactate, causing an underestimation of PPP activity.) Independent loss is expected because pyruvate kinase-catalyzed $^2$H loss is not stereospecific (Robinson, J. L. et al., J. Biol. Chem. 247:1096–1105 (1972)), and although there appears to be a large (approximately 8-fold) primary isotope effect in the loss of $^1$H versus $^2$H in pyruvate kinase-catalyzed pyruvate enolization (Saur, W. K. et al., Biochemistry 7:3537–3546 (1968)), secondary isotope effects (the effect of germinal $^2$H versus $^1$H on the rate of $^2$H loss) are quite small (approximately 10–15%) and would not significantly alter the rate of $^2$H loss from [H$^2$H$_2$]pyruvate versus [H$_2$$^2$H]pyruvate (Saur, W. K. et al., Biochemistry 7:3537–3546 (1968)). Non-random loss could occur, however, if both $^2$H atoms were lost simultaneously by some process. This does not occur in any reaction of glycolysis or the PPP, but the assumption may not be strictly valid if significant amounts of pyruvate enter the Krebs citric acid cycle and then leave via phosphoenolpyruvate carboxykinase.

The randomness of $^2$H loss was tested in an incubation with (6-$^{13}$C,6,6$^2$H$_2$)glucose (see Equations 27 and 31 below), and the effects of PMS (5 μM) on calculated PPP activity were tested in a parallel incubation with (1,6-$^{13}$C$_2$,6,6-$^2$H$_2$)glucose. In the absence of PMS, ($^{13}$C,$^2$H$_0$)lactate was 1.0% of total labeled lactate and P=4.0±0.4% with Equation 27, and ($^{13}$C,$^2$H$_0$)lactate was 3.3% of total labeled lactate and P=6.1±0.3% with Equation 31. With (1,6-$^{13}$C$_2$,6,6-$^2$H$_2$)glucose, P=2.5±0.7%. In the presence of PMS, P-33.7±0.7% with Equation 27 and P=37.7±0.6% with Equation 31, compared to P=36.9±0.9% with (1,6-$^{13}$C$_2$,6,6-$^2$H$_2$)glucose. Thus, although nonrandom $^2$H loss may introduce small errors in absolute quantitation of PPP activity, changes in PPP activity can be measured accurately with (1,6-$^{13}$C$_2$,6,6-$^2$H$_2$)glucose.

PPP activity in cultured rat 9L and human SF763 glioma cells was also determined by gas chromatography/mass spectrometry analysis of lactate extruded after incubation with (1,6-$^{13}$C$_2$,6,6-$^2$H$_2$)glucose Shown in Table 7 below, are PPP values under control conditions and maximum stimulation with phenazine methosulfate (PMS, 5 μM), tert-butyl hydroperoxide (t-BHP, 10 μM) and diamide (5 mM). Values under control conditions, of the glucose metabolised to lactate through the PPP, were 10.6±0.4% and 0.6±0.3% in 9L and SF763 cell lines, respectively. Stimulation of the PPP by PMS, t-BHP and diamide produced a dose response increase in activity, in both cell lines, until the maximum values shown in Table 7 were achieved.

TABLE 7

Measurement of PPP Activity In Response to Enzymatic Stimulation

| Cell line | Control | PMS | t-BHP | Diamide |
|---|---|---|---|---|
| SF763 | 0.6 ± 0.3 | 88.1 ± 0.3 | 51.2 ± 0.6 | 82.9 ± 0.7 |
| 9L | 10.8 ± 0.4 | 72.6 ± 0.4 | 52.9 ± 0.2 | 85.5 ± 0.3 |

*Average values are expressed as percentage (n = 4, ±SE) of glucose metabolized via the PPP relative to glycolysis.

(1,6-$^{13}$C$_2$,6,6-$^2$H$_2$)glucose was also used to monitor PPP activity in primary neuronal cultures. Measurements of PPP activity revealed basal levels between 0-2% of glucose metabolized to lactate via glycolysis. Addition of increasing concentrations of phenazine methosulphate (PMS), an artificial electron acceptor for NADPH, to the incubation medium for 30 minutes resulted in stimulation of the PPP in a dose dependent fashion to a maximum of 34±2% (n=3) with 25 μM PMS. Diamide, an oxidizing agent of reduced glutathione (GSH), stimulated the pathway to 20±2% (n=3) at 5 mM whereas H$_2$O$_2$ was found to stimulate the PPP to a maximal value of 11±1% (n=3) at 1 mM. These data indicate that glutathione peroxidase activity, rather than glucose 6-P dehydrogenase or glutathione reductase, may be rate-limiting for removal of hydrogen peroxide.

In order to determine whether exposure to N-methyl-D-aspartate (NMDA) results in intracellular formation of H$_2$O$_2$, primary neuronal cultures were incubated in the presence of 100 and 500 μM NMDA for 30 minutes. The PPP was stimulated to approximately 6% under both conditions, indicating that 100 μM NMDA is saturating. We observed that NMDA-induced PPP stimulation is slightly lower than the maximal stimulation with 1 mM H$_2$O$_2$. this difference can be attributed to the presence of a sub-population of glial cells in the culture, which will not be susceptible to NMDA. Thus, the observed PPP activity during NMDA exposure represents the weighted average of PPP in both cell populations. It is therefore suggested that NMDA causes maximal stimulation of the PPP in neurons, which may result in excess intracellular H$_2$O$_2$ with subsequent oxidative stress. Assessment of cell damage by a lactate dehydrogenase assay after 24 hours revealed similar toxicity in both cases.

Isotopic Dilution Study with (1,6-$^{13}$C$_2$,6,6-$^2$H$_2$)Glucose.

In order to establish that unlabeled lactate precursors would not interfere with PPP measurements using (1,6-$^{13}$C$_2$,6,6-$^2$H$_2$)glucose, 9L glioma cells were incubated with a KRB solution containing 4.4 mM (1,6-$^{13}$C$_2$,6,6-$^2$H$_2$)glucose (80%) and 1.1 mM unlabeled glucose (20%) with and without PMS.

To determine the effect of moderate isotope dilution on PPP measurements with (1,6-$^{13}$C$_2$,6,6-$^2$H$_2$)glucose, cultured 9L cells were incubated with 5.5 mM $^{13}$C$_2$,6,6-$^2$H$_2$)glucose (100), or with 4.4 mM (1,6-$^{13}$C$_2$,6,6-$^2$H$_2$)glucose (80) plus 1.1 mM unlabeled glucose (20). Baseline PPP activity of 6.4±0.3% and 5.8±0.7% increased o 43.5±1.8% and 41.8±3.6% in the presence of 5 μM PMS (Experiment 2 in Table 1 above). The presence of 20% unlabeled glucose therefore did not interfere with the measurement of PPP activity.

Time Course Study with (1,6-$^{13}$C$_2$,6,6-$^2$H$_2$)Glucose.

To demonstrate the ability to make repetitive measurements on a single set of cells, KRB (0.5 ml) containing 5.5 mM (1,6-$^{13}$C$_2$,6,6-$^2$H$_2$)glucose was added to and pipetted from 8 wells every hour during five hour time period. The condition for all of the well were kept identical except that in four of the wells, cells were exposed to 5 μM PMS during the third 1-hour time interval in order to stimulate PPP activity. After each one-hour incubation period, he buffer was moved and lyophilized for GO/MS analysis.

Figure 3:
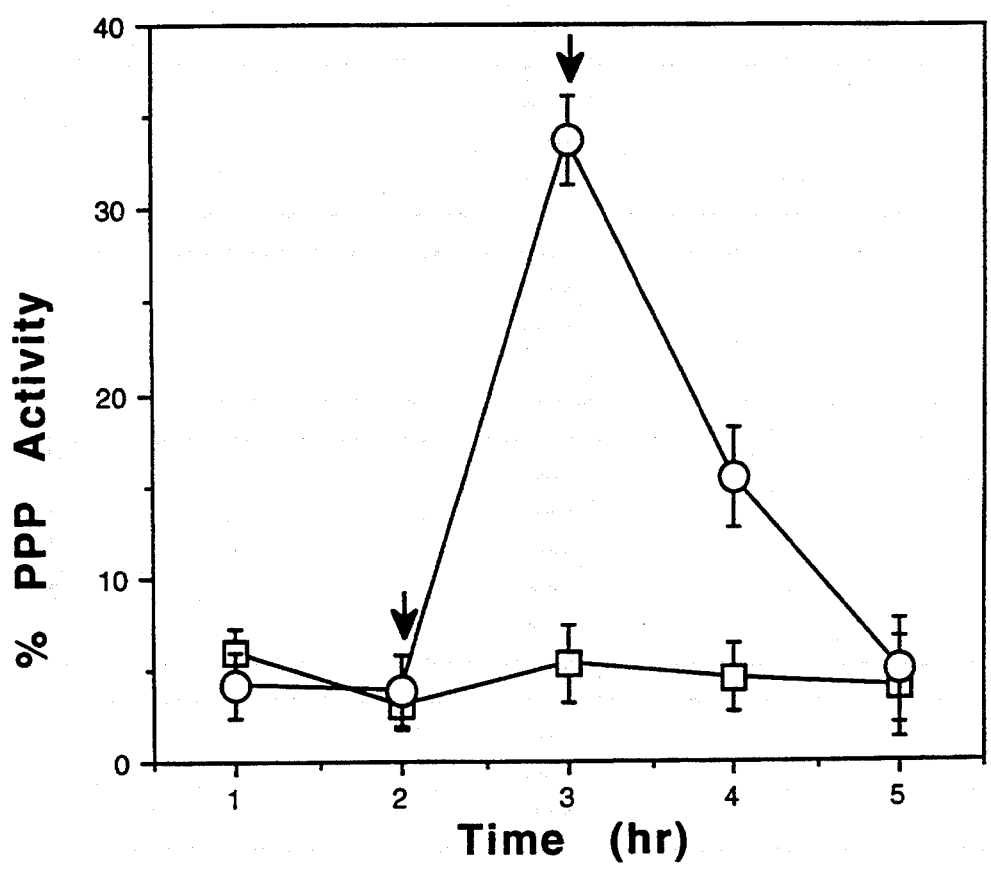
FIG. 3 is a graph depicting the time course of PPP activity in cultured 9L glioma cells.

In order to monitor the time course of PPP stimulation by PMS, incubation buffer containing 5.5 mM (1,6-$^{13}$C$_2$6,6-$^2$H$_2$)glucose was replaced every hour for five hours. In one set of four well, PMS w added during the third one-hour incubation period to stimulate PPP activity. PPP activity increased in the presence of PMS from 4.9±2.0% to 34.3±2.4% and then gradually declined to baseline levels after PMS was removed, while in a parallel set of four control wells, the PPP activity remained at 5.2-6.3%, a shown in FIG. 3. In FIG. 3, the PPP activity was quantitated by GC/MS analysis of lactate produced from the metabolism of (1,6-$^{13}$C$_2$,6,6-$^2$H$_2$)glucose in control cells (squares) and in cells exposed to 5 mM PMS between hours 2 and 3 (circles). The first and second downward pointing arrow in FIG. 3 indicate PMS addition and removal, respectively. This demonstrates the usefullness of (1,6-$^{13}$C$_2$,6,6-$^2$H$_2$)glucose in measuring PPP activity repetitively in a single sample of cultured cells.

SPECIFIC EXAMPLE 2

Construction of the Dialysis Probes.

The construction of microdialysis probe was accomplished as described previously by Robinson et al., Brain Res., 450:209 (1988). In brief, approximately 10 mm length of regenerated cellulose hollow fiber dialysis tubing was cemented into a 25-gauge stainless steel tube with 2-Ton clear epoxy (devcon) and allowed to dry for several hours. The dialysis fiber was trimmed to a length of 4 mm and the tip sealed with epoxy. The dialysis fiber used had a nominal molecular weight cut-off of 6000, an i.d. of 215 μm. This tubing was incorporated into the probe by slipping it through the 25 gauge stainless-steel cannula and into the dialysis chamber via a small hole pierced through the inlet tubing with a 26 gauge needle. All junctions were sealed with 2-Ton epoxy.

A guide cannula was surgically inserted, stereotaxically, on the dural surface of SF763 glioma cells and 9L glioma cells later implanted via the guide cannula at a pre-determined depth. Two days before anticipated microdialysis experiments, MRI was performed to determine to exact size and location of the glioma within the brain parenchyma. One day prior to a dialysis experiment, a probe was lowered into the tumor via the chronically implanted guide cannula and fixed in place. The rat was placed in a test chamber and the PE20 inlet tubing attached to a liquid swivel, which in turn was connected to a gas tight Hamilton 1000 series syringe mounted on a syringe pump. The perfusion fluid consisting of a modified Ringer's solution was pumped through the probe at a rate of 0.3 μl/min overnight. Sixteen to twenty hours later, a syringe containing 100 mM D-[1,6-$^{13}$C$_2$,6,6-$^2$H$_2$]glucose perfusion fluid was placed on the syringe pump and set to 1.0 μl/min. After a 60 min equilibration period, basal dialysate samples were continuously collected in mini-vials in 50 minute intervals over the 4.5 hour experimental time period. Samples were lyophilized, derivatized and analyzed by GC/MS.

In Vivo Studies.

Figure 4:
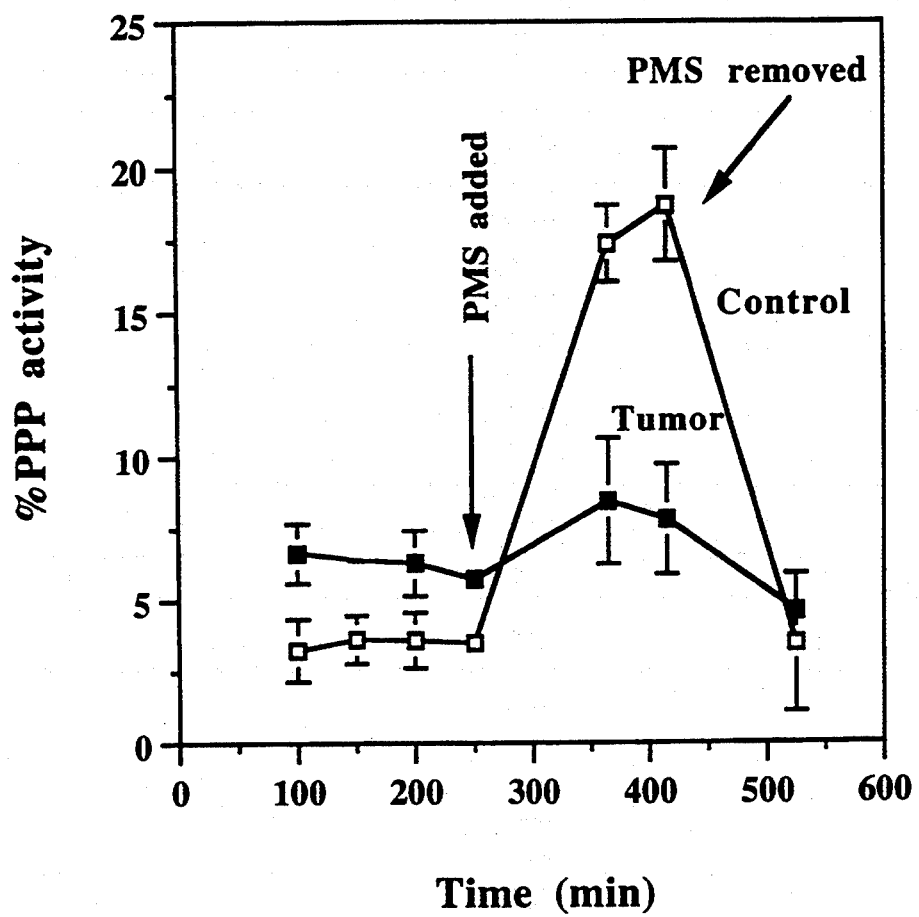
FIG. 4 is a graph depicting the time course of in vivo PPP activity in rat brain and intracerebral rat glioma.

D-(1,6-$^{13}$C$_2$,6,6-$^2$H$_2$)glucose was used in combination with intracerebral microdialysis and GC/MS techniques, for measuring the relative activities of glycolysis and the PPP in the forebrain and intracerebral 9L glioma in the conscious rat. Shown in FIG. 4 are the in vivo PPP measurements for rat brain (closed triangles) and an intracerebral rat glioma (open squares) from administering D-(1,6-$^{13}$C$_2$,6,6-$^2$H$_2$)glucose via an implanted microdialysis probe. GC/MS analysis of extracellular lactate, collected in the dialysate over 50 minute intervals, revealed a baseline PPP activity of 3.5±0.2% and 6.2±0.4% of glucose metabolized to lactate in normal rat brain and in 9L glioma, respectively. Addition of 501 μM phenazine methosulfate (PMS) to the perfusate at 250 minutes, in brain and glioma resulted in an increased PPP activity of 18.1±2.2% and 7.4±1.7%, respectively. PPP activity returned to basal levels upon removal of PMS from the perfusate under both conditions. The higher basal PPP activity of the glioma compared to normal brain is most likely associated with an elevated NADPH requirement necessary for the increased lipid biosynthesis in the proliferating neoplasm. This study represents the first time-solved in vivo measurements of the PPP in living tissue. Furthermore, this technique provides a unique opportunity to measure the PPP in localized regions of the brain (and glioma) in a conscious rat. Sample collection using microdialysis together with high GC/MS sensitivity allow for dynamic changes in PPP activity to be followed in a single animal.

D-$(1,6-^{13}C_2,6,6-^2H_2)$glucose is used to quantitate the baseline activity of the PPP in intracranial SF763 gliomas and utilize chemical stimulants of the PPP to determine the degree of inhibition achieved following systemic administration of an antioxidant enzyme inhibitor using microdialysis techniques. Microdialysis samples are collected in 30 minute intervals from intracranial SF763 gliomas for 4 time points (2.0 hours total time). For all in vivo PPP experiments, the dialysate for the first 2 time points contains only D-$[1,6-^{13}C_2,6,6-^2H_2]$glucose to quantitate baseline glioma PPP activity. During the 3rd and 4th time points, an oxidative stimulant is added to the dialysate to stimulate the activity of the PPP to probe maximum metabolic turnover.

The individual groups in these studies are described in Table 8 below:

TABLE 8

| Assay for Enzymatic Stimulation of PPP Activity | | |
|---|---|---|
| Group 1 | D-$[1,6-^{13}C_2,6,-^2H_2]$glucose + | diamide |
| Group 2 | D-$[1,6-^{13}C_2,6,-^2H_2]$glucose + | PMS |
| Group 3 | D-$[1,6-^{13}C_2,6,-^2H_2]$glucose + | t-BHP |
| Group 4 | D-$[1,6-^{13}C_2,6,-^2H_2]$glucose + | F-DHEA + | PMS |
| Group 5 | D-$[1,6-^{13}C_2,6,-^2H_2]$glucose + | 2,4-DHB + | diamide |
| Group 6 | D-$[1,6-^{13}C_2,6,-^2H_2]$glucose + | BSO + | diamide |
| Group 7 | D-$[1,6-^{13}C_2,6,-^2H_2]$glucose + | mercaptocuccinate + | t-BHP |
| Group 8 | D-$[1,6-^{13}C_2,6,-^2H_2]$glucose + | AT (Enzyme assay from tumor extract) | |

Groups 1, 2 and 3 are designed to determine the minimum concentration of each chemical stimulant needed to achieve maximum stimulation of the PPP in vivo using 3 different concentrations for each of the following stimulants (3 rats per each concentration): diamide (0.1, 1.0, & 10 mM), PMS (0.1, 1.0 & 10 mM) and t-BHP (1.0, 10, & 100 mM). If maximal stimulation of the PPP activity is not achieved, then additional experiments are done with higher concentrations of stimulant until increasing stimulant concentration produces no further increase in PPP activity. Once the concentration of each stimulant needed to achieve maximum stimulation is determined, it is used to test the effectiveness of enzyme inhibitors in groups 4–8. Groups 4–8 are comprised of 6 rats/group pre-exposed to one of each of the five enzymatic inhibitors. Group 4 receives dehydroepiandrosterone (F-DHEA) (300 mg/kg,i.p.) 2 hours before initiation of microdialysis experiments. Group 5 receives 2.4 dihydroxybenxylamine (2,4-DHB) (400 mg/kg,i.p.) 1 hour before microdialysis experiment. Group 6 receives S-(n-Butyl)homocysteine (BSO 2.5 mmol/kg,i.p.) for 4 doses at 12 hour intervals, with concomitant availability in acidified drinking water (pH 3.0) at a concentration of 20 mM as previously described by Lippitz et al., Neurosurg., 26:255 (1990). Group 7 rats receive mercaptosuccinate (500mg/kg,i.p.) 3 hour prior to initiation of microdialysis experiment. Group 8 receives 3-amino-1,2,4-triazole (AT) (1 g/kg,i.p.) 3 hours prior to initiation of microdialysis experiment. Aragon et al., Biochem. Pharmacol. 42:699 (1991). Again, because there are no cofactors common with the PPP and catalase, a separate biochemical analysis (Cohen et al., Anal. Biochem. 34:30 (1970)) for inhibition of catalase is accomplished.

The effectiveness of each inhibitor is evaluated by stimulating the inhibition process involved and comparing the percent stimulation achieved with the value obtained without the presence of inhibitor. The degree of reduction in PPP activity is reflective of the cells reduced capacity for detoxifying the oxidative stress which should correlate with the extent of enzyme inhibition achieved.

SPECIFIC EXAMPLE 3

Complex Models.

A more complex model like that of Landau and Bartsch (Landau, B. R. et al., J. Biol. Chem. 241:741–749 (1966)), incorporating glycogen and galactose synthesis, removal of pentose phosphates for nucleotide synthesis, removal of dihydroxyacetone phosphate for synthesis of phosphoglycerides and triacylglycerols (via sn-glycerol 3-phosphate), and numerous exchange reactions is not necessary in most cases. (It may be necessary in special cases such as liver, adipose tissue (Katz, J. et al., J. Biol. Chem. 241:727–740 (1966)), and lactating mammary gland.) Such a complex model was developed for studies where the distribution of $^{14}C$ from [2-$^{14}C$]glucose in hexose and triose products was analysed, and the PPP as a fraction of total glucose utilization was desired. Labeled and unlabeled lactate from glucose labeled in the C1 and/or C6 positions are compared herein and only the ratio of PPP to glycolysis is measured.

Removal of Glc-6-P, dihydroxyacetone phosphate, and ribose-5-P for synthesis of glycogen (and galactose), glycerides, and nucleotides, respectively, is expected to be a small percentage of total glucose utilization under most circumstances, and the molecules removed from both PPP and the glycolytic pathway will be at least partly equilibrated with both C1 and C6 of glucose. If recycling is small, then Glc-6-P removed for glycogen and galactose synthesis contains primarily the intact, fully labeled glucose molecule and thus will not affect the pattern of lactate labelling. If recycling is extensive, the lost Glc-6-P will have a labelling pattern similar to that of Fru-6-P, Which has an excess of C6 due to loss of C1 in the PPP; PPP activity in this case would be slightly underestimated. Transaldolase, however, can catalyse the incorporation of C1 from glucose into the C6 position of Fru-6-P. Landau, B. R. et al., J. Biol. Chem. 241:741–749 (1966). This tends to equilibrate the C6 position of Fru-6-P with the isotopic label of glyceraldehyde-3-P, which is identical to the labelling pattern in lactate (see FIG. 1). With or without recycling, the effect of glycogen and galactose synthesis on the calculated value of P should be small.

Dihydroxyacetone phosphate will probably be labeled slightly more with C1 of glucose than with C6 due to incomplete equilibration of triose phosphates by triose phosphate isomerase, but there will be some, and probably extensive, equilibration with glyceraldehyde-3-P. Incomplete equilibration would lead to an overestimation of PPP activity if dihydroxyacetone-P is utilized for lipid synthesis.

Removal of pentose phosphates labeled with C6 of glucose would give an underestimation of the PPP pathway. However, while the net flux of carbon atoms is from hexose phosphate to pentose phosphate through the oxidative branch, and from pentose phosphate to glycolytic intermediates through the nonoxidative branch, there may be extensive equilibration of pentose phosphates with glycolytic products via the nonoxidative branch. Katz, J. et al., Biochemistry 6:2227–2247 (1967). For example, there is significant synthesis of [2-$^{14}$C]ribose from [2-$^{14}$C]glucose in muscle (Green, M. R. et al., Arch. Biochem. Biophys. 111:569–575 (1965)) and bacteria (Katz, J. et al., Biochemistry 6:2227–2247 (1967)), and of [1-$^{14}$C]deoxyribose from [1-$^{14}$C]glucose in bacteria. Katz, J. et al., Biochemistry 6:2227–2247 (1967). Thus, much of the pentose phosphate removed for nucleotide synthesis will be labeled with the labelling pattern of Fru-6-P and glyceraldehyde-3-P, not exclusively with C6, and will therefore have a greatly reduced effect on PPP measurement.

In summary, PPP activity may be slightly underestimated in the presence of glycogen, galactose, and nucleotide synthysis, and slightly overestimated in the presence of lipid synthesis.

Assumptions and Conventions.

In all glucoses labeled with two or more labels in one position (for example, 6-$^{13}$C,6,6-$^2$H$_2$ or 1-$^{13}$C,1-$^2$H), it is assumed that fractional enrichment in each label is independent of enrichment in any other label(s) in the same position, but the two $^2$H atoms on C6 of glucose may have different fractional enrichments. If enrichment is not independent, the formulas must be modified to reflect the actual isotope distribution. It is not necessary that C1 labels be independent of C6 labels. For example, (6-$^{13}$C,1,6,6-$^2$H$_3$)glucose could be replaced by a mixture of (1-$^2$H)glucose and (6-$^{13}$C,6,6-$^2$H$_2$)glucose, but not by a mixture of (6-$^{13}$C)glucose and (1,6,6-$^2$H$_3$)glucose.

Lactate isotopes are often represented by a shorthand notation, for example, $^2$H$_2^{13}$C=(3-$^{13}$C,3,3-$^2$H$_2$)lactate. Initial isotope enrichments are represented by, for example, $L_{H6}$=enrichment of $^2$H attached to C6 of glucose. Terms of the form $(1-L_C)/L_C$ appear frequently and will be abbreviated as $\Lambda_C=(1-L_C)/L_C$.

In the following formulas, it is assumed that carbon labels are not lost (except by the PPP), though $^2$H may be exchanged for $^1$H. If $^2$H and $^{13}$C labels are independently distributed, then the amount of (3-$^{12}$C, 3-$^2$H$_n$)lactate can be calculated from the amount of (3-$^{13}$C, 3-$^2$H$_n$)lactate with the equation $$^2H_n{}^{12}C = (^2H_n{}^{13}C)\Lambda_C \qquad (2)$$

where $\Lambda_C$ is defined above and $L_C$ is the fractional enrichment of $^{13}$C in the position of interest.

After the GC/MS peaks have been resolved into individual isotope components, the values of P, T and E may be calculated from the formulas in Table 3 and Table 4 above:

$$P = 1 - [C1]\text{lactate}/[C6]\text{lactate} \qquad (3)$$

$$P = 1 - R_1/R_6 \qquad (4)$$

$$P/3 \leq T \leq P/(3-2P) \qquad (5)$$

$$E = r_6 + T - 1. \qquad (6)$$

LOSS of $^2$H Labels.

The use of a $^2$H label introduces a new factor: the $^2$H may be removed by exchange with water. This complicates measurement of PPP activity but may allow monitoring of other enzyme activities in cells. For example, pyruvate kinase can catalyze the loss of $^2$H from the methyl group of pyruvate. Robinson, J. L. et al., J. Biol. Chem. 247:1096–1105 (1972). This exchange can also occur nonenzymatically, and other enzymes may also catalyze this exchange. Such exchange from triose derivatives will be referred to as $1-\kappa$, where $\kappa$ is the probability that an individual $^2$H atom is retained when the final lactate molecule is observed. Such an exchange will have an equal effect on pyruvate (and lactate) containing a $^2$H atom from either C1 or C6 of glucose.

Phosphomannose isomerase, however, can catalyze an exchange of the $^2$H label initially on C1 of glucose via Fru-6-P⇌Man-6-P without affecting any $^2$H attached to C6 of glucose. Saur, W. K. et al., Biochemistry 7:3529–3536 (1968) and Saur, W. K. et al., Biochemistry 7:3537–3546 (1968). This exchange is referred to as $1-\mu$, where $1-\mu$ is the probability that an individual $^2$H atom will be lost in a phosphomannose isomerase-catalyzed reaction. During the metabolism of (1-$^2$H)glucose, this exchange results in the formation of unlabeled lactate rather than (3-$^2$H)lactate through glycolysis. This result would be indistinguishable from loss of the C1 label through PPP activity. Although this complicates measurement of PPP activity, it allows an indirect measurement of phosphomannose isomerase activity. The parameters $\kappa$ and $\mu$ can be determined by GC/MS analysis after incubations with (6-$^{13}$C,6,6-$^2$H$_2$)glucose and (1-$^{13}$C,1-$^2$H)glucose.

When glucose contains two $^2$H atoms in the C6 position, one or both of these may be missing in the original labeled glucose or may be lost during production of lactate. If the absence or loss of $^2$H in each site is independent of the other site, then the relative amounts of $^2$H$_2$-, $^2$H$_1$-, and $^2$H$_0$-labeled molecules can be calculated from the following formulas, where $L_{H6a}$ and $L_{H6b}$ are the mole fractions of $^2$H attached to C6 of glucose and $\kappa$ is the mole fraction of $^2$H in each site that is retained during metabolism ($\kappa=1$ for glucose, $\kappa\leq 1$ for lactate):

$$(^2H_2) = \kappa^2 L_{H6a} L_{H6b} \qquad (7)$$

$$(^2H_1) = \kappa L_{H6a}(1-\kappa L_{H6b}) + \kappa L_{H6b}(1-\kappa L_{H6a}) \qquad (8)$$

$$(^2H_0) = (1-\kappa L_{H6a})(1-\kappa L_{H6b}). \qquad (9)$$

The value of $\kappa$ can be calculated from the ratio:
$$S_6 = (^2H_1{}^{13}C)/^2H_2{}^{13}C) \qquad (10)$$

$$S_6 = (1-\kappa L_{H6a})/(\kappa L_{H6a}) + (1-\kappa L_{H6b})/(\kappa L_{H6b}) \qquad (11)$$

$$\kappa = (L_{H6a} + L_{H6b})/[L_{H6a}L_{H6b}(S_6+2)]. \qquad (12)$$

The amount of lactate that has lost two $^2$H atoms can be calculated from the amounts that lost no $^2$H atoms or one $^2$H atom:

$$(^2H_0)=(^2H_2)(1-\kappa L_{H6a})(1-\kappa L_{H6b})/(\kappa^2 L_{H6a}L_{H6b}). \quad (13)$$

If $L_{H6a}=L_{H6b}$, Equation 13 simplifies to:

$$(^2H_0)=(^2H_1)^2/[4(^2H_2)]. \quad (14)$$

The loss of $^2$H from C1 of glucose can be calculated from the following formulas, where $L_{H1}$ is the mole fraction of $^2$H in glucose, $1-\kappa$ is the mole fraction of $^2$H that is lost from triose derivatives, and $1-\mu$ is the mole fraction of $^2$H that is lost from C1 of glucose before formation of triose derivatives, presumably in reactions catalyzed by phosphomannose isomerase:

$$S_1 \equiv (^2H^{13}C)/(^2H^{13}C + {}^1H^{13}C) = \mu\kappa L_{H1} \quad (15)$$

$$\mu\kappa = S_1/L_{H1}. \quad (16)$$

If $\kappa$ is known, $\mu$ can be calculated.
Measurements with (1-$^{13}$C)Glucose and (6-$^{13}$C)Glucose.

In parallel incubations with (1-$^{13}$C)glucose and (6-$^{13}$C)glucose, the m/z 219 peak corresponds to unlabeled lactate and the m/z 220 peak corresponds to (3-$^{13}$C)lactate. With (1-$^{13}$C)glucose, $$R_1 = (m/z\ 220)/[(m/z\ 219 + m/z\ 220)L_{C1}]. \quad (17)$$

With (6-$^{13}$C)glucose, $$R_6 = (m/z\ 220)/[(m/z\ 219 + m/z\ 220)L_{C6}] \quad (18)$$

$$r_6 = L_{C6}[(m/z\ 219)-(m/z\ 220)\Lambda_{C6}]/(m/z\ 220). \quad (19)$$

The values of P, T and E can be calculated from Equations 4 through 6.
Measurements with (1,5,6-$^{13}$C$_3$)Glucose.

Because [C1]lactate produced from (1,5,6-$^{13}$C$_3$)glucose contains a single $^{13}$C atom while [C6]lactate contains two $^{13}$C atoms, they correspond to m/z 220 and m/z 221, respectively, after appropriate corrections for isotopic enrichment (Table 6).

$$[C6]lactate = (m/z\ 221)/(L_{C5}L_{C6}) \quad (20)$$

$$[C1]lactate = [(m/z\ 220) = (m/z\ 221)(\Lambda_{C6}+\Lambda_{C6})]/L_{C1} \quad (21)$$

$$r_6 = \frac{\{(m/z\ 221) + (m/z\ 220) + (m/z\ 219) - [C6]lactate\}}{[C6]lactate} \quad (22)$$

Measurements with (6-$^{13}$C,6,6-$^2$H$_2$)Glucose and (1-$^{13}$C,1-$^2$H)Glucose.

The isotopic labelling pattern in lactate produced from (6-$^{13}$C,6,6-$^2$H$_2$)glucose is given in Table 9 below. In Table 9, the amount of lactate with each isotopic composition reflects incomplete fractional enrichment and possible metabolic $^2$H loss. For lactate produced from C1 of glucose, see Table 10 below.

$$^2H_2{}^{13}C = m/z\ 222 \quad (23)$$

$$^2H_2{}^{12}C = (m/z\ 222)\Lambda_{C6} \quad (24)$$

$$^2H_1{}^{13}C = (m/z\ 221) - {}^2H_2{}^{12}C \quad (25)$$

$$^2H_1{}^{12}C = (^2H_1{}^{13}C)\Lambda_{C6} \quad (26)$$

The value of $\kappa$ can be calculated from Equation 12.

$$^2H_0{}^{13}C = {}^2H_2{}^{13}C(1-\kappa L_{L6a})/(\kappa^2 L_{H6a}L_{H6b}) \quad (27)$$

$$^2H_0{}^{12}C = (^2H_0{}^{13}C)\Lambda_{C6} \quad (28)$$

$$R_6 = \frac{[(m/z\ 222) + (m/z\ 221) + (m/z\ 220) + {}^2H_0^{12}C]}{[(m/z\ 222) + (m/z\ 221) + (m/z\ 220) + (m/z\ 219)]} \quad (29)$$

$$r_6 = \frac{(m/z\ 219) - {}^2H_0^{12}C}{[(m/z\ 222) + (m/z\ 221) + (m/z\ 220) + {}^2H_0^{12}C]} \quad (30)$$

TABLE 9

Isotope Enrichment In Lactate Produced from C6 of (6-$^{13}$C,6,6,$^2$H$_2$)Glucoses With Different Enrichments In the Two $^2$H Positions

| m/z | Isotope | Amount In Lactate |
|---|---|---|
| 222 | $^2H_2{}^{13}C$ | $(\kappa L_{H6a})(\kappa L_{H6b})L_{C6}$ |
| 221 | $^2H_2{}^{12}C$ | $(\kappa L_{H6a})(\kappa L_{H6b})(1-L_{C6})$ |
| 221 | $^2H_1{}^{13}C$ | $[\kappa L_{H6a}(1-\kappa L_{H6b}) + \kappa L_{H6b}(1-\kappa L_{H6a})]L_{C6}$ |
| 220 | $^2H_1{}^{12}C$ | $[\kappa L_{H6a}(1-\kappa L_{H6b}) + \kappa L_{H6b}(1-\kappa L_{H6a})](1-L_{C6})$ |
| 220 | $^2H_0{}^{13}C$ | $(1-\kappa L_{H6a})(1-\kappa L_{H6b})L_{C6}$ |
| 219 | $^2H_0{}^{12}C$ | $(1-\kappa L_{H6a})(1-\kappa_{H6b})(1-L_{C6})$ |

Equation 27 assumes independent loss of the two $^2$H atoms on C6 of glucose and can be used for other (6-$^{13}$C,6,6-$^2$H$_2$)glucoses even when C1 is also isotopically labeled. In the absence of a C1 label, the assumption of independent loss can be checked by comparing Equation 27 with the following formula:

$$^2H_0{}^{13}C_2(observed) = (m/z\ 220) - {}^2H_1{}^{12}C. \quad (31)$$

The isotopic labelling pattern in lactate produced from (1-$^{13}$C,1-$^2$H)glucose is shown in Table 10 below. The amount of lactate with each isotopic composition reflects incomplete fractional enrichment and possible metabolic $^2$H loss but does not reflect loss of C1 by PPP activity.

$$^2H^{13}C = m/z\ 221 \quad (32)$$

$$^2H^{12}C = {}^2H^{13}C\Lambda_{C1} \quad (33)$$

$$^1H^{13}C = m/z\ 220 - {}^2H^{12}C \quad (34)$$

$$^1H^{12}C = (^1H^{13}C)\Lambda_{C1} \quad (35)$$

$$R_1 = \frac{[(m/z\ 221) + (m/z\ 220) + {}^1H^{12}C]}{[(m/z\ 221) + (m/z\ 220) + (m/z\ 219)]} \quad (36)$$

With $R_1$ and $R_6$ from Equations 36 and 29, respectively, $P = 1 - R_1/R_6$. To calculate $\mu$, $S_1$ can be calculated from Equation 15 with the isotopomers in Equations 32 and 34, and $\kappa$ can be found from a parallel incubation with (6-$^{13}$C,6,6-$^2$H$_2$)glucose.

TABLE 10

Isotope Enrichment In Lactate Produced from C1 of Isotopically Substituted Glucose Molecules

| m/z | Isotope | Amount In Lactate |
|---|---|---|
| (1-$^{13}$C,1-$^2$H)glucose: | | |
| 221 | $^2H^{13}C$ | $\mu\kappa L_{H1}L_{C1}$ |
| 220 | $^2H^{12}C$ | $\mu\kappa L_{H1}(1-L_{C1})$ |

TABLE 10-continued

Isotope Enrichment In Lactate Produced from C1 of Isotopically Substituted Glucose Molecules

| m/z | Isotope | Amount In Lactate |
|---|---|---|
| 220 | $^1H^{13}C$ | $L_{C1}(1-\mu\kappa L_{H1})$ |
| 219 | $^1H^{12}C$ | $(1-L_{C1})(1-\mu\kappa L_{H1})$ |
| (6-$^{13}$C,1,6,6-$^2$H$_3$)glucose: | | |
| 220 | $^2H_1^{12}C$ | $\mu\kappa L_{H1}$ |
| 219 | $^2H_0^{12}C$ | $1-\mu\kappa L_{H1}$ |
| (1,6-$^{13}$C$_2$,6,6-$^2$H$_2$)glucose: | | |
| 220 | $^2H_0^{13}C$ | $L_{C1}$ |
| 219 | $^2H_0^{12}C$ | $1-L_{C1}$ |

Measurements with (6-$^{13}$C,1,6,6-$^2$H$_3$)Glucose.

Metabolism of (6-$^{13}$C,1,6,6-$^2$H$_3$)glucose yields six distinct isotopomers of lactate (Tables 9 and 10). The formulas for (6-$^{13}$C,6,6-$^2$H$_2$)glucose (Equations 23–28) can be used for the six isotopomers from C6 of glucose, but two isotopomers must be specified as containing C6:

$$^2H_1^{12}C[C6] = (^2H_1^{13}C)\Lambda_{C6} \quad (37)$$

$$^2H_0^{12}C[C6] = (^2H_0^{13}C)\Lambda_{C6} \quad (38)$$

Two isotopomers come from C1 of glucose:

$$^2H_1^{12}C[C1] = (m/z\ 220) - {}^2H_1^{12}C[C6] - {}^2H_0^{13}C \quad (39)$$

$$^2H_0^{12}C[C1] = (^2H_1^{12}C[C1])[1-\mu\kappa L_{H1}]/[\mu\kappa L_{H1}] \quad (40)$$

where the product $\mu\Lambda$ can be determined from a study with (1-$^{13}$C,1-$^2$H)glucose (Equation 21). If there is no $^2$H exchange catalyzed by phosphomannose isomerase, $\mu=1$, and $\kappa$ can be calculated for (6-$^{13}$C,1,6,6-$^2$H$_3$)glucose as it was for (6-$^{13}$C,6,6H$_2$)glucose. To determine P from Equation 3, add the isotopomers in Equations 23–25, 27, 37 and 38 to yield total [C6]lactate and add the isotopomers in Equations 39 and 40 to yield total [C1]lactate.

Measurements with (1,6-$^{13}$C$_2$,6,6-$^2$H$_2$)Glucose.

Metabolism of (1,6-$^{13}$C$_2$,6,6-$^2$H$_2$)glucose will yield six distinct isotopomers of lactate (Tables 9 and 10). The six isotopomers from C6 of glucose can be calculated with the formulas for (6-$^{13}$C,6,6$^2$H$_2$)glucose but the $^2$H$_0$ isotopomers must be specified as containing C6:

$$^2H_0^{13}C[C6] = {}^2H_2^{13}C(1-\kappa L_{H6a})(1-\kappa L_{H6b})/(\kappa^2 L_{H6a}L_{H6b}) \quad (41)$$

$$^2H_0^{12}C[C6] = (^2H_0^{13}C[C6])\Lambda_{C6}. \quad (42)$$

Two isotopomers come from C1 of glucose:

$$^2H_0^{13}C[C1] = (m/z\ 220) - {}^2H_1^{12}C - {}^2H_0^{13}C[C6] \quad (43)$$

$$^2H_0^{12}C[C1] = (^2H_0^{13}C[C1])\Lambda_{C1}. \quad (44)$$

To determine P, add the isotopomers in Equations 23 through 26, 41 and 42 to yield total [C6]lactate and add the isotopomers in Equations 43 and 44 to yield total [C1]lactate.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims. All publications are herein incorporated by reference.

We claim:

1. A method of assaying for the presence of labeled lactate produced by an enzyme system wherein lactate is derived from glucose, and wherein the label is derived from an isotopically substituted glucose, the method comprising the steps of:
   a) providing an isotopically substituted glucose comprising D-(1,6-$^{13}$C$_2$,6,6-$^2$H$_2$)glucose;
   b) administering the substituted glucose to the system;
   c) providing means for detecting labeled lactate; and
   d) detecting the presence of labeled lactate derived from the substituted glucose.

2. The method of claim 1, wherein the system comprises a cell culture.

3. The method of claim 1, wherein the system comprises a cell or tissue sample from an organism.

4. The method of claim 1, wherein the system comprises a living organism.

5. The method of claim 1, wherein the method further comprises the step of:
   e) measuring the labeled lactate of step d).

6. A method of measuring pentose phosphate pathway activity in an enzyme system, the method comprising the steps of:
   a) providing an isotopically substituted glucose comprising D-(1,6-$^{13}$C$_2$,6,6-$^2$H$_2$)glucose;
   b) administering the substituted glucose to the system;
   c) providing means for quantifying labeled lactate derived from the substituted glucose through pentose phosphate pathway activity; and
   d) quantifying the labeled lactate to measure pentose pathway activity.

7. The method of claim 6, wherein the system comprises an in vitro cell culture.

8. The method of claim 6, wherein the system comprises a cell or tissue sample from an organism.

9. The method of claim 6, wherein the system comprises a living organism.

* * * * *